(12) United States Patent
Schmitz et al.

(10) Patent No.: US 8,072,613 B2
(45) Date of Patent: Dec. 6, 2011

(54) SYSTEM FOR MEASURING THE INNER SPACE OF A CONTAINER AND METHOD OF PERFORMING THE SAME

(75) Inventors: Joerg Schmitz, Moers (DE); Rolf Lamm, Aachen (DE); Christoph Carlhoff, Willich (DE)

(73) Assignee: Specialty Minerals (Michigan) Inc., Bingham Farms, MI (US)

( * ) Notice: Subject to any disclaimer, the term of this patent is extended or adjusted under 35 U.S.C. 154(b) by 0 days.

(21) Appl. No.: 12/731,188

(22) Filed: Mar. 25, 2010

(65) Prior Publication Data

US 2011/0235052 A1 Sep. 29, 2011

(51) Int. Cl.
*G01B 11/24* (2006.01)
(52) U.S. Cl. .......... 356/608; 266/99; 266/100; 356/601; 356/4.01; 356/5.15
(58) Field of Classification Search .................. 266/99, 266/100; 356/601–608, 4.01–5.15
See application file for complete search history.

(56) References Cited

U.S. PATENT DOCUMENTS

| | | | |
|---|---|---|---|
| 4,138,888 A | 2/1979 | Linder | |
| 5,212,738 A * | 5/1993 | Chande et al. ................ | 356/601 |
| 6,780,351 B2 | 8/2004 | Wirth, Jr. | |
| 6,837,616 B2 | 1/2005 | Ignatowicz | |
| 6,922,251 B1 | 7/2005 | Kirchhoff et al. | |
| 7,230,724 B2 | 6/2007 | Jokinen et al. | |
| 7,330,242 B2 * | 2/2008 | Reichert et al. .............. | 356/4.01 |
| 2005/0263945 A1 | 12/2005 | Kirchhoff et al. | |
| 2009/0237678 A1 | 9/2009 | Brzoska et al. | |

FOREIGN PATENT DOCUMENTS

| | | |
|---|---|---|
| EP | 0 121 617 A1 | 10/1984 |
| JP | 60-235005 | 11/1985 |
| WO | WO 94/06032 A1 | 3/1994 |
| WO | WO 03/081157 A1 | 10/2003 |

* cited by examiner

*Primary Examiner* — Gregory J Toatley
*Assistant Examiner* — Iyabo S Alli
(74) *Attorney, Agent, or Firm* — Derek S. Jessen; Leon Nigohosian, Jr.

(57) ABSTRACT

A system and method for measuring the inner space of a container provides for the measurement of the wear of the lining of a container such as a torpedo ladle optionally while the ladle is still hot. The interior lining of the container is scanned by a scanner head from a first position in the container which is at an angle relative to the vertical axis of the container. The scanner head is placed in a second position in the container at an angle relative to the vertical axis of the container and from the second position the scanner head scans the portions of the interior lining of the container which were not scanned during the first position scan. By comparing the scanning measurements of the lining from the first position scan and the second position scan after the container has been loaded and unloaded with an initial reference measurement of the lining the wear of the lining can be measured.

20 Claims, 11 Drawing Sheets

SYSTEM FOR MEASURING THE INNER SPACE OF A CONTAINER AND METHOD OF PERFORMING THE SAME

BACKGROUND

Devices are used for measuring buildings, ground structures, machines and plants etc. In general, these systems comprise a measuring head wherein a measuring beam is deviated at a high speed and in a fan-like manner. Deviation of the measuring beam can be achieved by pivoting mirrors, rotating mirror wheels or the like. Often it is desired to measure inner rooms of buildings, caverns, and caves, when excavating tunnels or mines etc. Applications under especially difficult conditions are in steel industry when measuring converters and transport vessels or containers for molten pig iron or steel.

For operational reasons, molten metals are often transported from a place of production to a processing place. In steel industry, appropriate vessels, so-called torpedo ladles, are used to bring liquid pig iron from a blast furnace to a converter and, optionally, from it to a foundry, particularly to continuous casting machines, where slabs are cast as a starting material for mill processing. These torpedo ladles, which are able to contain several hundred of tons of iron melt or steel melt, have a lining which constitutes a thermal isolation and, at the same time, protects the steel jacket of the vessel against the action of the melt. As in steel converters, linings of such torpedo ladles are subjected to wear, and the result can be, in particular, that individual bricks of the lining break out. Since such damage can seriously affect the security and the environment, the lining of this transport equipment has to be inspected, repaired or replaced on a regular basis which, of course, causes high expenses. When carrying out such an inspection, the torpedo ladle (or any other vessel for materials) has to be cooled down and, afterwards, has to be heated slowly up to working temperature. This results in a considerable interruption of operation that causes correspondingly high costs.

SUMMARY

A system and method are disclosed which can provide precise measurement of an inner space and/or lining of a container. By comparing measurements of the lining of the container before and after operation measurement of the lining is carried out and changes in the lining of the container, such as by wear and breaking out of bricks, can be determined in an exact manner. Thus, repair of the lining can be carried out only when actually necessary.

In some embodiments, the interior lining of the container is scanned by a scanner head which is mounted at an angle relative to the vertical axis of the container. The scanner head scans the lining of the vessel from a first position in the container. The scanner head which is mounted at an angle relative to the vertical axis of the container is then placed in a second position in the container and from the second position the seamier head scans at least portions of the interior lining of the container which were not scanned during the first position scan. By comparing the scanning measurements of the lining from the first position scan and the second position scan after the container has been loaded and unloaded with an initial reference measurement of the lining the wear of the lining can be measured.

In some embodiments, the interior lining of the container is scanned by a scanner head which is provided on a rotating means and the scanner is at an angle relative to the vertical axis of the container. The scanner head scans the lining of the vessel from a first position in the container. The rotating means rotates the scanner head and the scanner head scans from the second position at least portions of the interior lining of the container which were not scanned during the first position scan. By comparing the scanning measurements of the lining from the first position scan and the second position scan after the container has been loaded and unloaded with an initial reference measurement of the lining the wear of the lining can be measured.

In some embodiments, the interior lining of the container is scanned by a scanner head which is provided on a support means or lance such that the scanner is at an angle relative to the vertical axis of the container. The scanner head can be arranged such that the scanner head is aligned with the lance. In an embodiment the scanner head is not at an angle with respect to the lance. The scanner head scans the lining of the vessel from a first position in the container. The lance together with the scanner head is placed in a second position and the scanner head scans at least portions of the interior lining of the container which were not scanned during the first position scan. By comparing the scanning measurements of the lining from the first position scan and the second position scan after the container has been loaded and unloaded with an initial reference measurement of the lining the wear of the lining can be measured.

BRIEF DESCRIPTION OF THE DRAWINGS

The invention will now be described in connection with reference to the drawings in which.

DETAILED DESCRIPTION OF THE PREFERRED EMBODIMENTS

Figure 1:
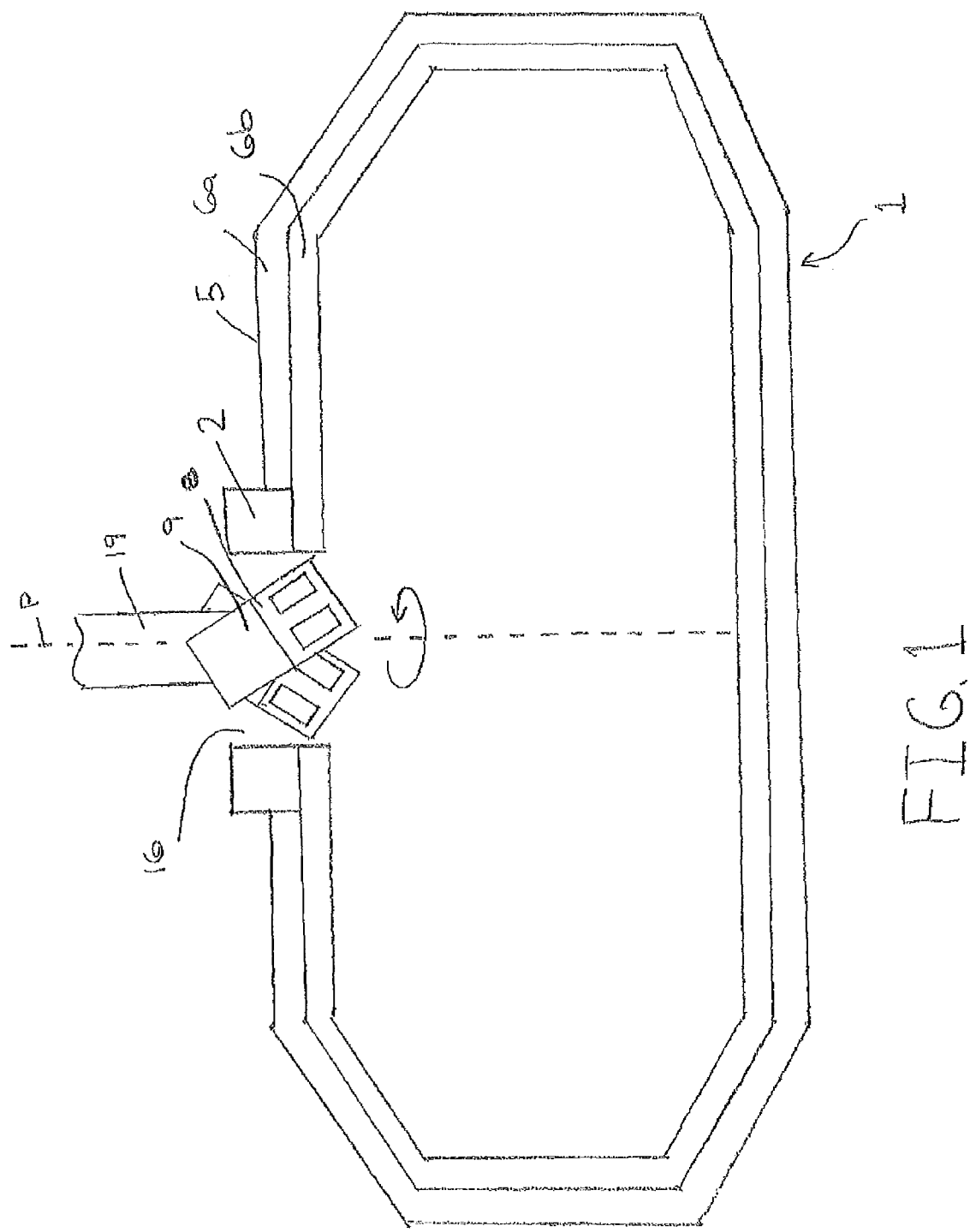
FIG. 1 shows schematically an embodiment of the system for measuring the inner space of a container according to the present invention illustrating the laser scanner being provided in the opening of a container.

In FIG. 1, a torpedo ladle 1 is schematically illustrated in a cross-sectional view. An exemplary torpedo ladle 1 comprises a cylindrical center portion having a filling and emptying neck 2. On both sides end portions join the center portion. The torpedo ladle 1 is rotatably supported. The torpedo ladle 1 has a steel jacket 5. The inner space has a lining which can include or consist of two layers, i.e. an inner wear layer 6a and an outer security lining 6b. For emptying the torpedo ladle 1, the torpedo ladle 1 is rotated relative to the horizontal axis of the torpedo ladle.

In some embodiments of the system for measuring wear of the present invention, the interior of the tube 19 conduits for a cooling medium and/or a pressurized air conduit for cooling the measuring head 8 are also led. The whole installation can be controlled by a control and data cable which is connected to an electronic calculator which, in turn, calculates either on-line or off-line a 3-D model of the interior of the torpedo ladle 1 from the measured data determined by an evaluating unit, and also stores the data suitably in an affiliated memory.

In order to facilitate introducing the appliance into the filling neck 2 of the torpedo ladle 1, the tube 19 can be rotatable around the major axis P of the tube 19 or manipulator as seen in FIG. 1 to thus orient the measuring head with respect to the torpedo ladle 1. The scanning of the contour of the lining of the torpedo ladle can be done by laser measuring scanner, here, comprising measuring head 8 and base 9 on which measuring head 8 is mounted is rotated by rotation of tube 19.

Precise orientation of the measuring system at the torpedo ladle 1 can, for example, be important when a comparison and formation of the difference between an actual recording and an older recording are desired. Instead of orienting the measuring system mechanically, it is also possible to, for example, orient the system appropriately with respect to the torpedo ladle 1 by measuring reference points.

FIG. 1 shows the limited range of motion of the measuring head 8 and base 9 after rotating head 8 and base 9 on tube 19 due to the narrow opening 16 of the torpedo ladle 1.

Figure 2:
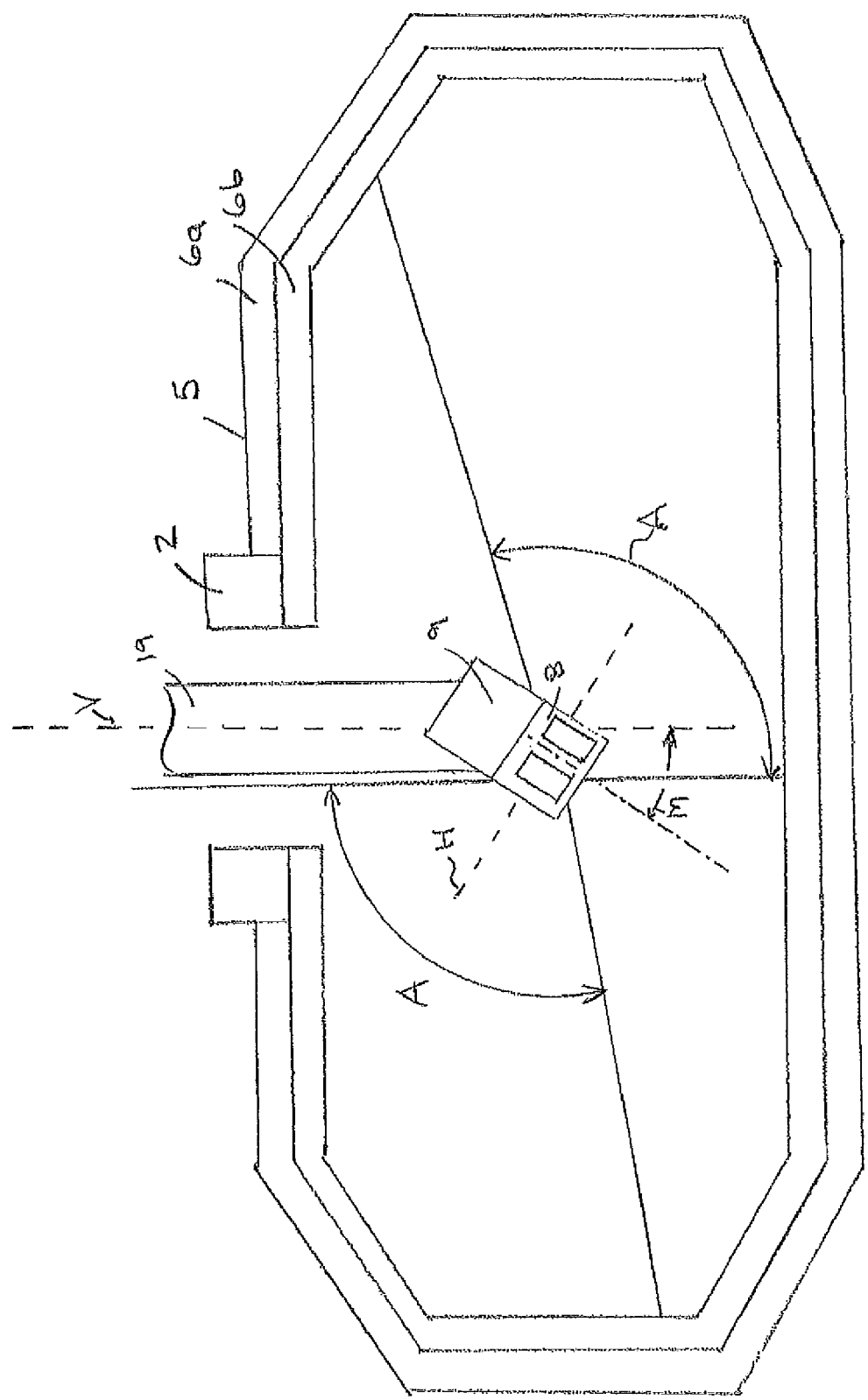
FIG. 2 shows schematically the embodiment of the system for measuring the inner space of a container according to FIG. 1 illustrating the first position scan of the scanning means.

FIG. 2 shows the tube 19 inserted inside a metallurgical vessel in a first position, here, a torpedo ladle 1 such that the measuring head 8 scans the inside contour of the inner lining 6b of the ladle with the angle A which is formed by the upper boundary of the scanning laser and the lower boundary of the scanning laser to obtain a first scan. The upper boundary of the scanning laser of measuring head 8 can be about positive (+) 50 degrees from an axis H of the measuring head 8. The lower boundary of the scanning laser can be about minus (−) 50 degrees from the major axis of the measuring head 8. Accordingly, angle A can be about 100 degrees total.

As seen in FIG. 2, the measuring head 8 can be at an angle M with respect to the vertical axis V of the torpedo ladle 1 of about positive (+) 30 degrees to positive (+) 60 degrees, or in some embodiments +35 to +45 degrees. The measuring head 8 is at a first position from which a portion of the inside contour of the torpedo ladle 1 is scanned to obtain a first scan by rotation of measuring head 8. The measuring head 8 can rotate 360 degrees relative to base 9.

Figure 3:
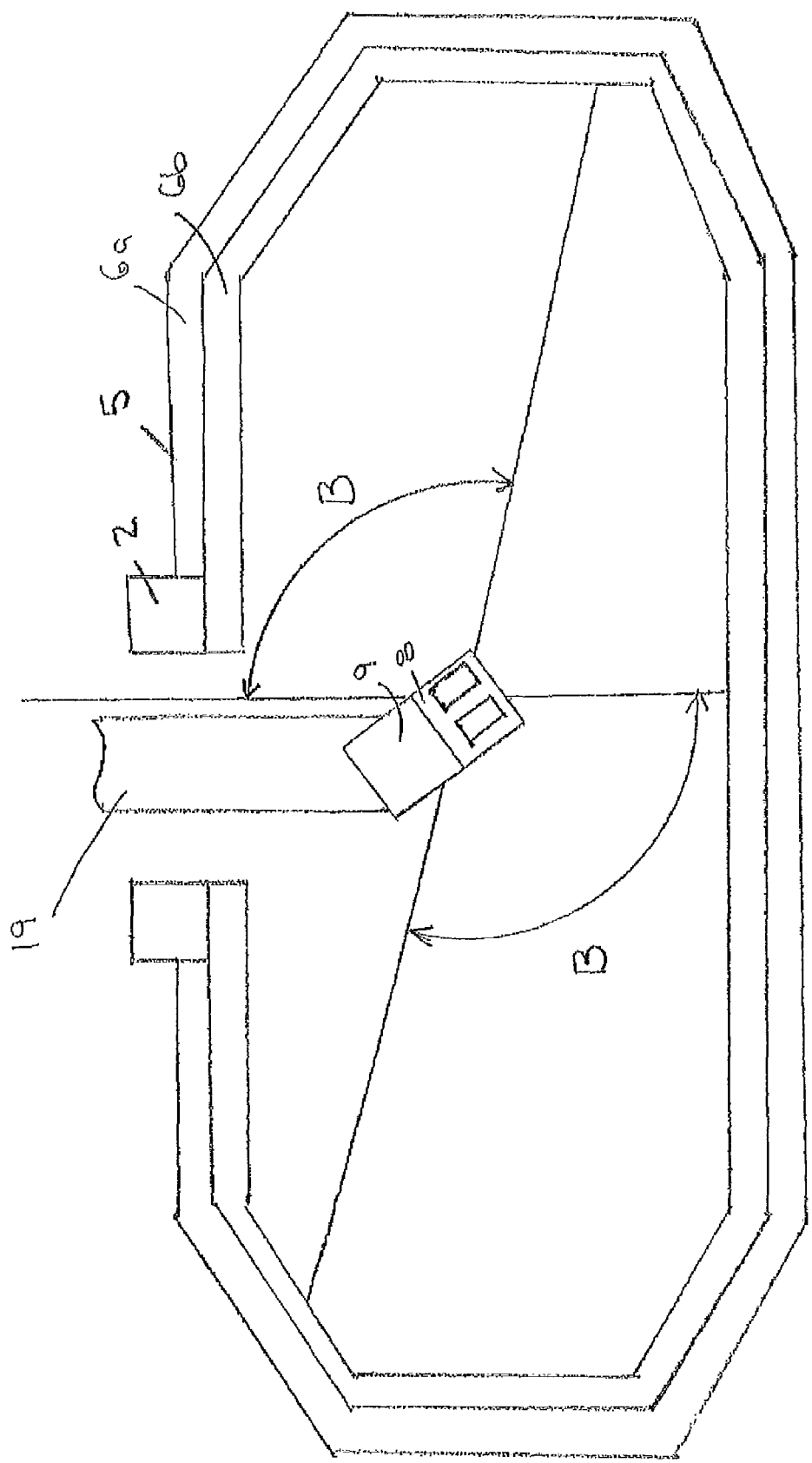
FIG. 3 shows schematically the embodiment of the system for measuring the inner space of a container according to FIG. 1 illustrating the second position scan of the scanning means.

Later, as seen in FIG. 3 the manipulator or tube 9 is rotated approximately 180 degrees and positions the measuring head 8 in a second position inside the torpedo ladle 1 also at an angle M with respect to the vertical axis V of the torpedo ladle 1 of about positive (+) 30 degrees to positive (+) 60 degrees, or in some embodiments +35 to +45 degrees. The measuring head 8 is then at a second position from which a portion of the inside contour of the torpedo ladle 1 is scanned through angle B to obtain a second scan of the inside contour of the torpedo ladle 1 by rotation of measuring head 8 through 360 degrees relative to base 9.

As can be seen in FIGS. 2 and 3, portions of the lining of the torpedo ladle 1 which were not scanned in the first position scan are scanned during the second position scan. Also, some portions of the lining which were scanned in the first scan can be scanned again in the second scan. In the system for measuring wear in the refractory lining of a metallurgical vessel, here, a torpedo ladle 1, of the present invention an electronic calculator combines the first scan and second scan to obtain a combined measurement of the contour of the lining. The calculations are performed either on-line or off-line. A 3-D model of the interior of the torpedo ladle 1 from the data resulting from the first position scan and the second position scan is calculated by an evaluating unit. The data can be stored in a memory unit.

A comparison of the difference between an actual measurement of the contour of the lining of the torpedo ladle 1 and a previous measurement of the contour of the lining of the torpedo ladle 1 can result in a determination of the condition of the lining.

In some embodiments, the lining of the torpedo ladle 1 can be scanned from at least three different positions in the torpedo ladle 1 to ensure that an accurate scanning of the lining takes place. At least one of the positions from which the lining is scanned is inside of the torpedo ladle 1.

Figure 4:
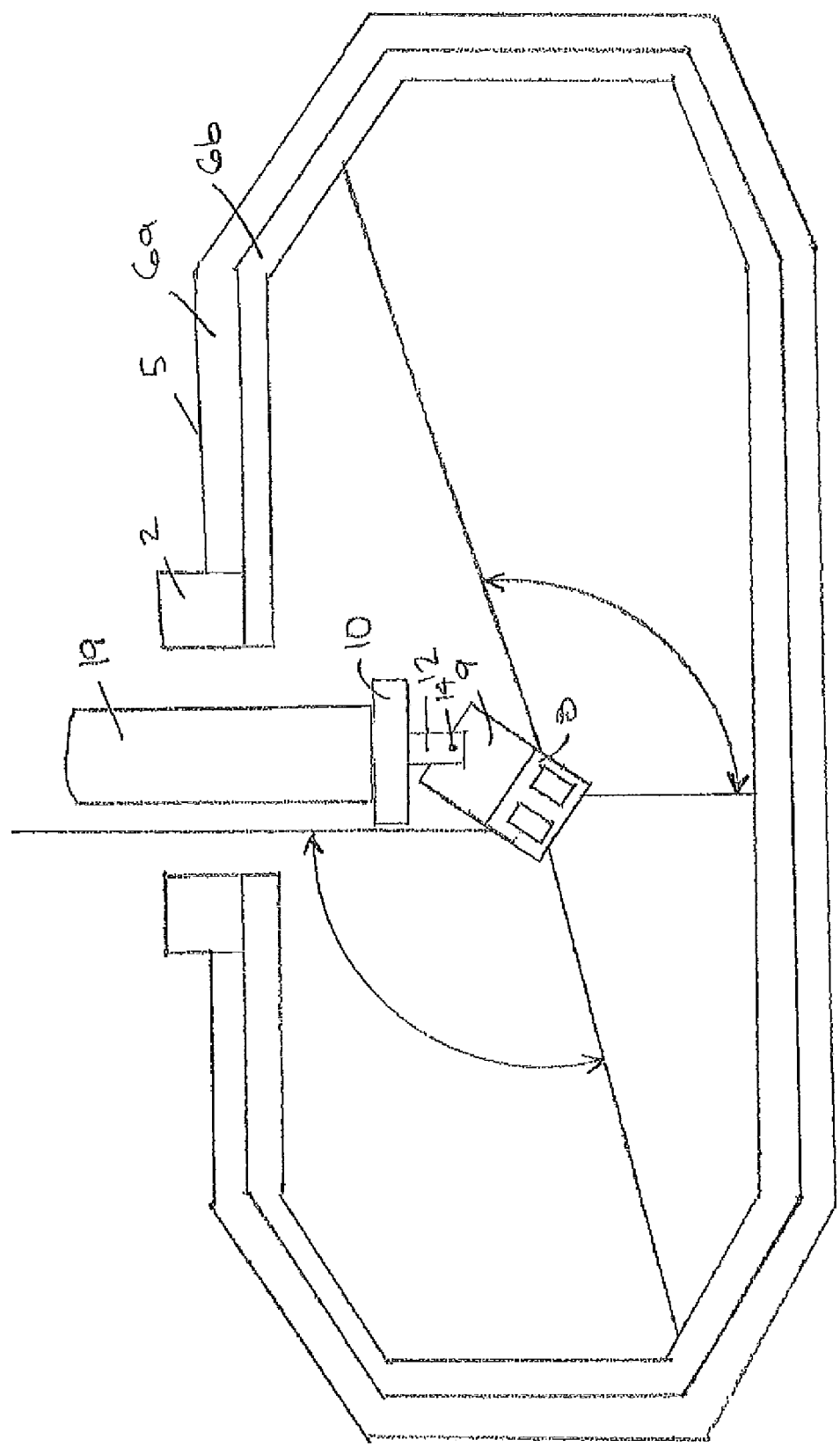
FIG. 4 shows schematically another embodiment of the system of the present invention for measuring the inner space of a container illustrating the first position scan of the scanning means.
Figure 5:
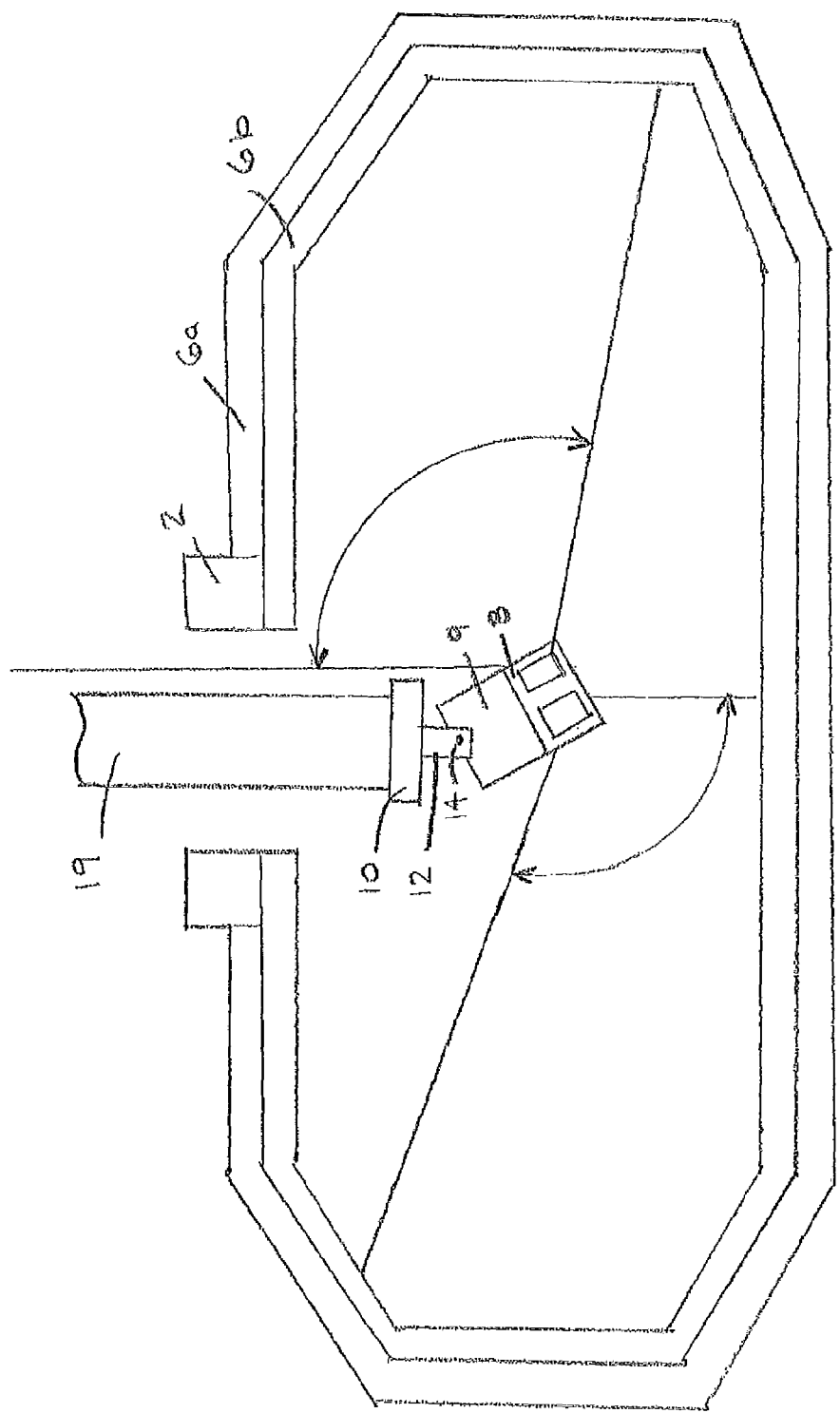
FIG. 5 shows schematically the embodiment of FIG. 4 of the system for measuring the inner space of a container illustrating the second position scan of the scanning means.

In other embodiments of the invention, the measuring head 8 and base 9 can be connected to a means for rotating the measuring head 8 and base 9, here a plate 10 from a first position from which a portion of the inner lining of the torpedo ladle 1 is scanned as seen in FIG. 4 to a second position from which the inner lining of the torpedo ladle 1 is scanned as seen in FIG. 5. Bracket 12 having pin 14 provides a means for connecting the base 9 to rotating plate 10 such that the measuring head 8 and base 9 can be placed at an angle relative to the axis of the torpedo ladle 1. In FIG. 5, the rotation of rotating plate 10 about 165 to 195 degrees, preferably 180 degrees, permits the scanning of the inner lining of the torpedo ladle 1 from the second position at which another portion of the lining of the torpedo ladle 1 is scanned which includes portions of the torpedo ladle 1 which were not scanned from the first position. Accordingly, the first scan and second scan are combined as described above to obtain a combined measurement of the contour of the lining.

Figure 6:
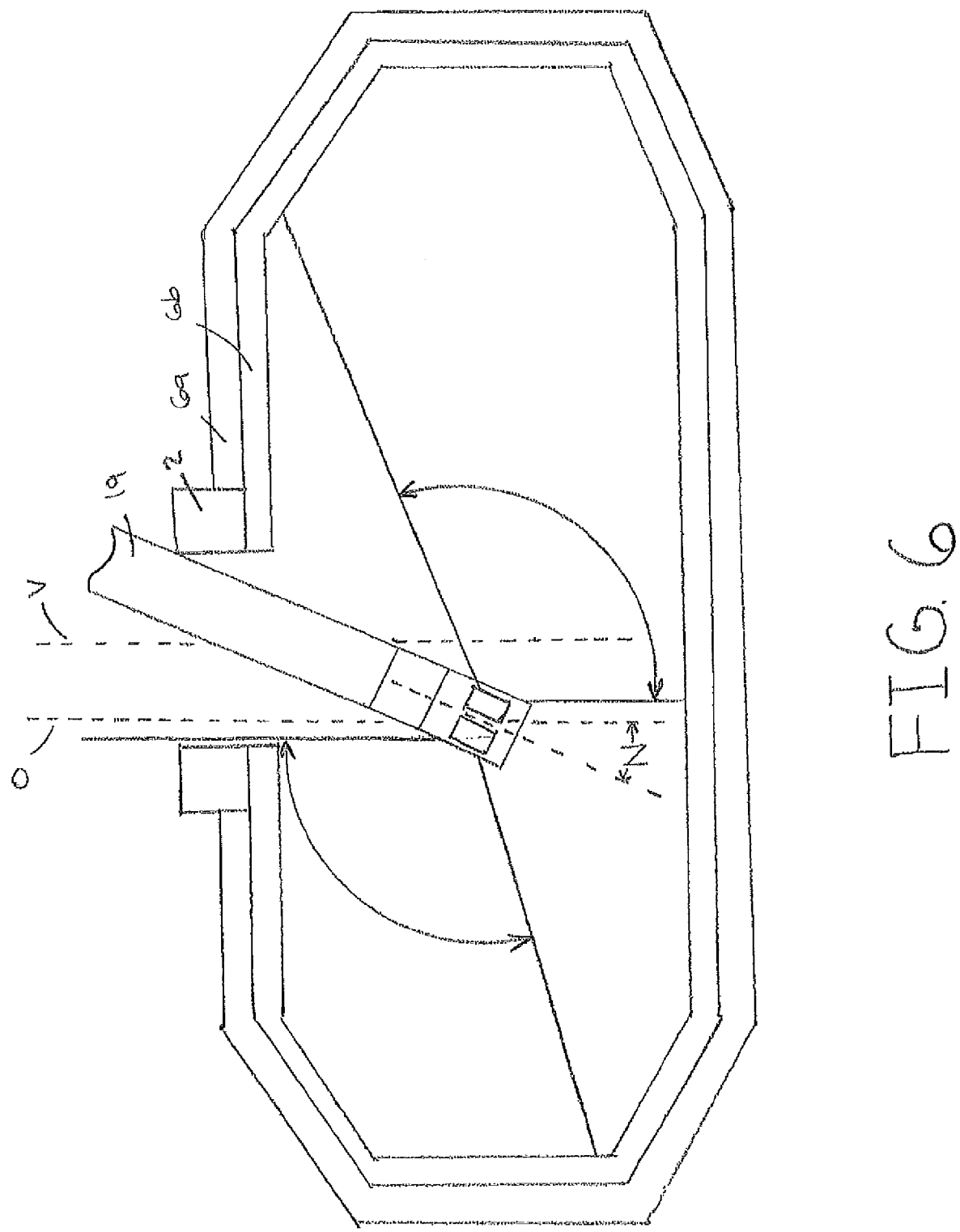
FIG. 6 shows schematically another embodiment of the system of the present invention for measuring the inner space of a container illustrating the first position scan of the scanning means.
Figure 7:
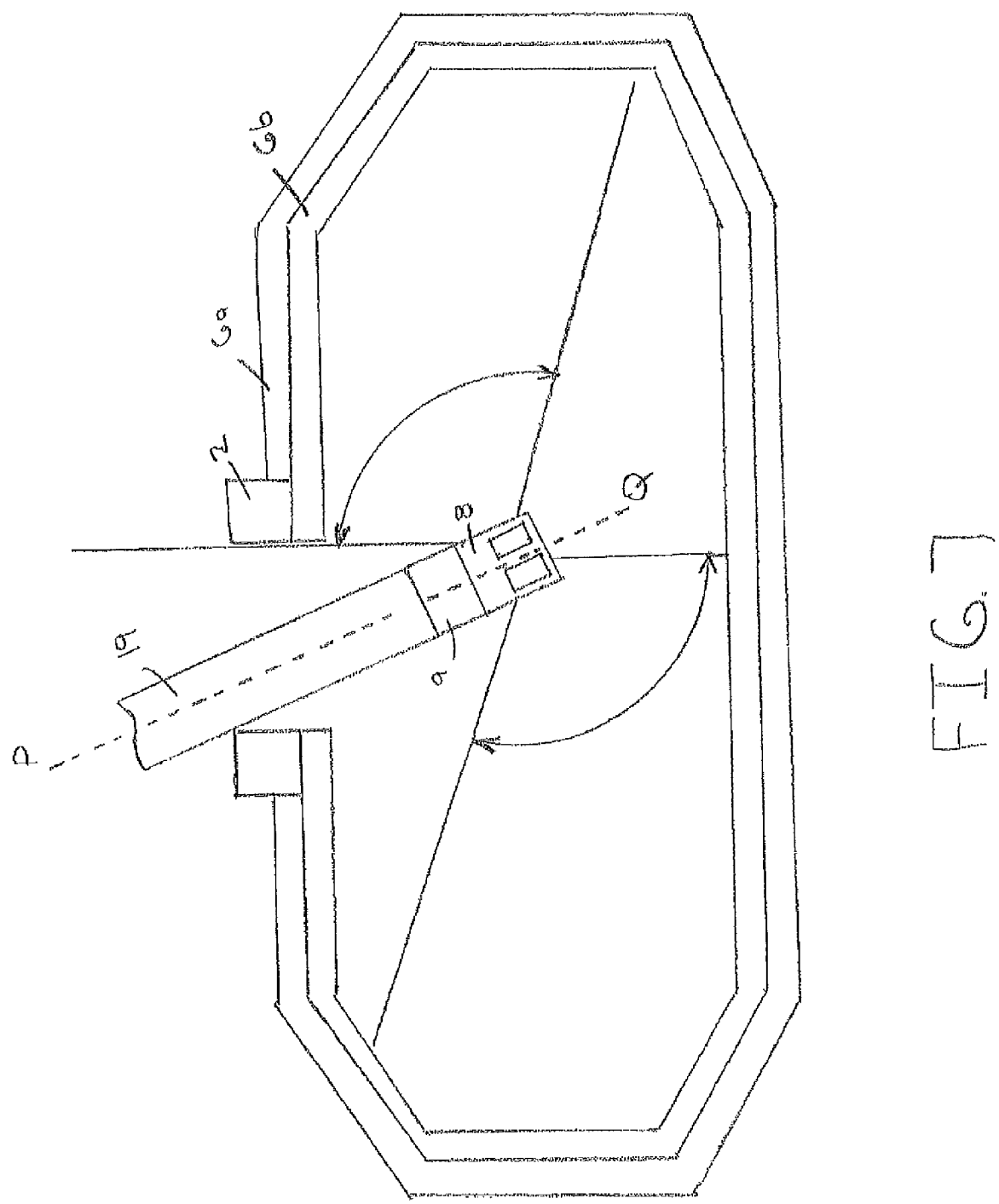
FIG. 7 shows schematically the embodiment of FIG. 6 of the system for measuring the inner space of a container illustrating the second position scan of the scanning means.

In some embodiments, as seen in FIG. 6 the tube or manipulator itself to which the measuring head 8 and base 9 are connected can be provided at a first angle with respect to the axis of the metallurgical vessel or torpedo ladle 1 such that the laser scanner is positioned at a first angle to obtain a first scan from a first position of a portion of the lining of the torpedo ladle 1. The measuring head 8 can be at an angle N with respect to the vertical axis V of the torpedo ladle 1 or as shown a line O parallel to vertical axis V of the torpedo ladle 1 of about positive (+) 30 degrees to positive (+) 60 degrees, or in some embodiments +35 to +45 degrees. Then, as shown in FIG. 7, the tube 19 or manipulator itself can be provided at a second angle with respect to the axis of the metallurgical vessel or torpedo ladle 1 such that the laser scanner is positioned at a second angle to obtain a second scan from a second position which includes portions of the torpedo ladle 1 which were not scanned from the first position. The major axis P of the tube 19 can be coaxial with the axis Q around which the measuring head 8 rotates as seen in FIG. 7. Accordingly, the first scan and second scan are combined as described above to obtain a combined measurement of the contour of the lining.

Figure 8:
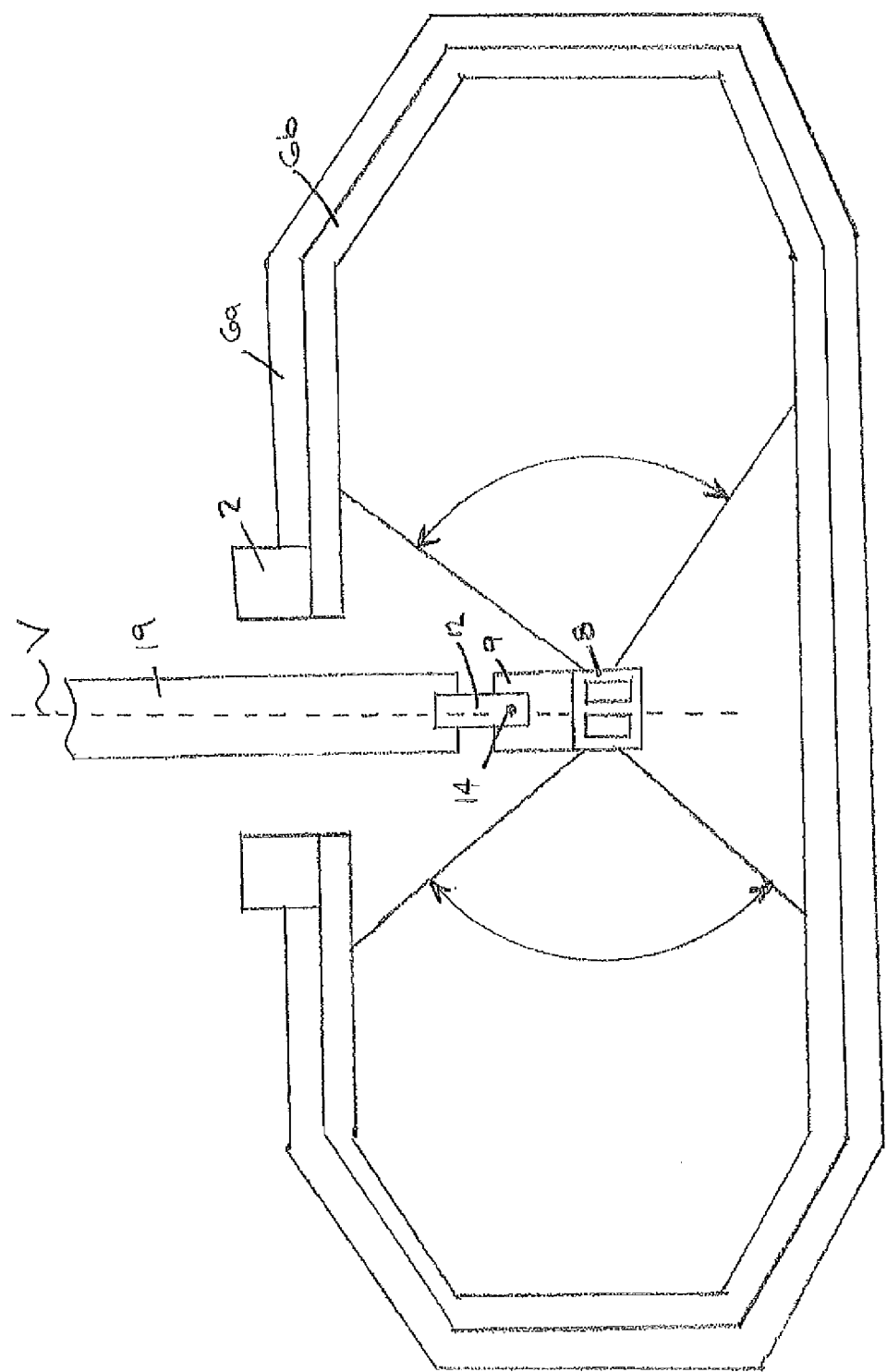
FIG. 8 shows schematically another embodiment of the system of the present invention for measuring the inner space of a container illustrating the first position scan of the scanning means.

In some embodiments, the contour of the lining of the torpedo ladle 1 can be scanned from a position outside of the torpedo ladle 1 as seen in FIGS. 8, 9 and 10 or FIGS. 8, 9 and 11. The measuring head 8 and base 9 can be connected to a means for rotating the base 9 and measuring head 8, here, a plate 10 from a first position from which the inner lining 6*b* of the torpedo ladle 1, primarily the end portions of the torpedo ladle 1, are scanned as seen in FIG. 8. The laser scanner or measuring head 8 can be at an angle of 0 to 15 degrees, preferably 0 degrees with respect to the vertical axis V of the torpedo ladle 1.

Figure 9:
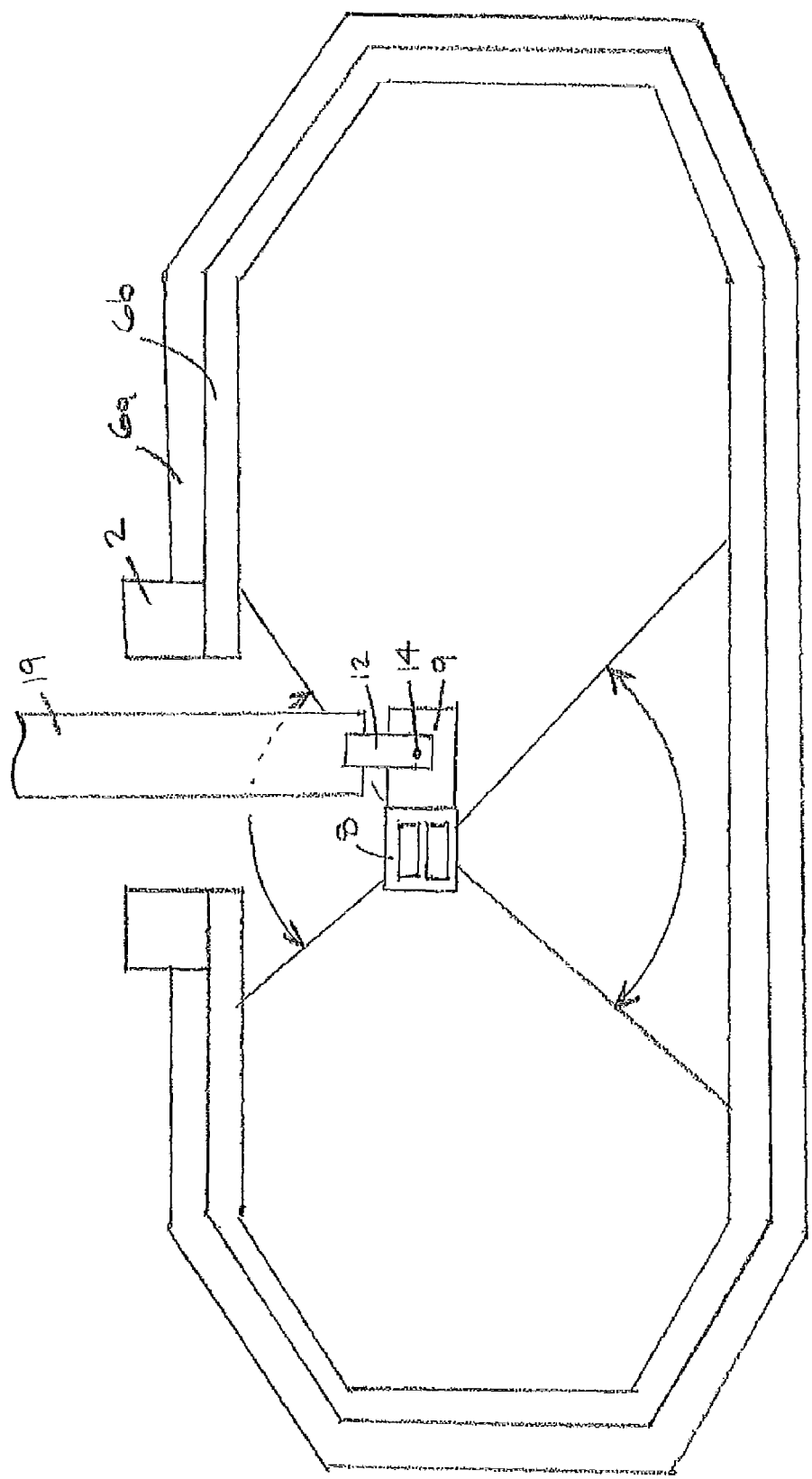
FIG. 9 shows schematically the embodiment of FIG. 8 of the system for measuring the inner space of a container illustrating the second position scan of the scanning means.

The laser scanner or measuring head 8 is then moved to a second position from which the inner lining 6*b* of the torpedo ladle 1 is scanned as seen in FIG. 9. Bracket 12 is connected to the base 9 such that the measuring head 8 and base 9 can be placed at the desired angle relative to the axis of the torpedo ladle 1. In FIG. 9, the rotation or pivoting of the laser scanner on bracket 10 to a position of from about 75 to 90 degrees, preferably 90 degrees relative to the axis V of the torpedo ladle 1, permits the scanning of the inner lining 6*b* of the torpedo ladle 1 from the second position at which portions of the torpedo ladle 1 which were not scanned from the first position are scanned.

Figure 10:
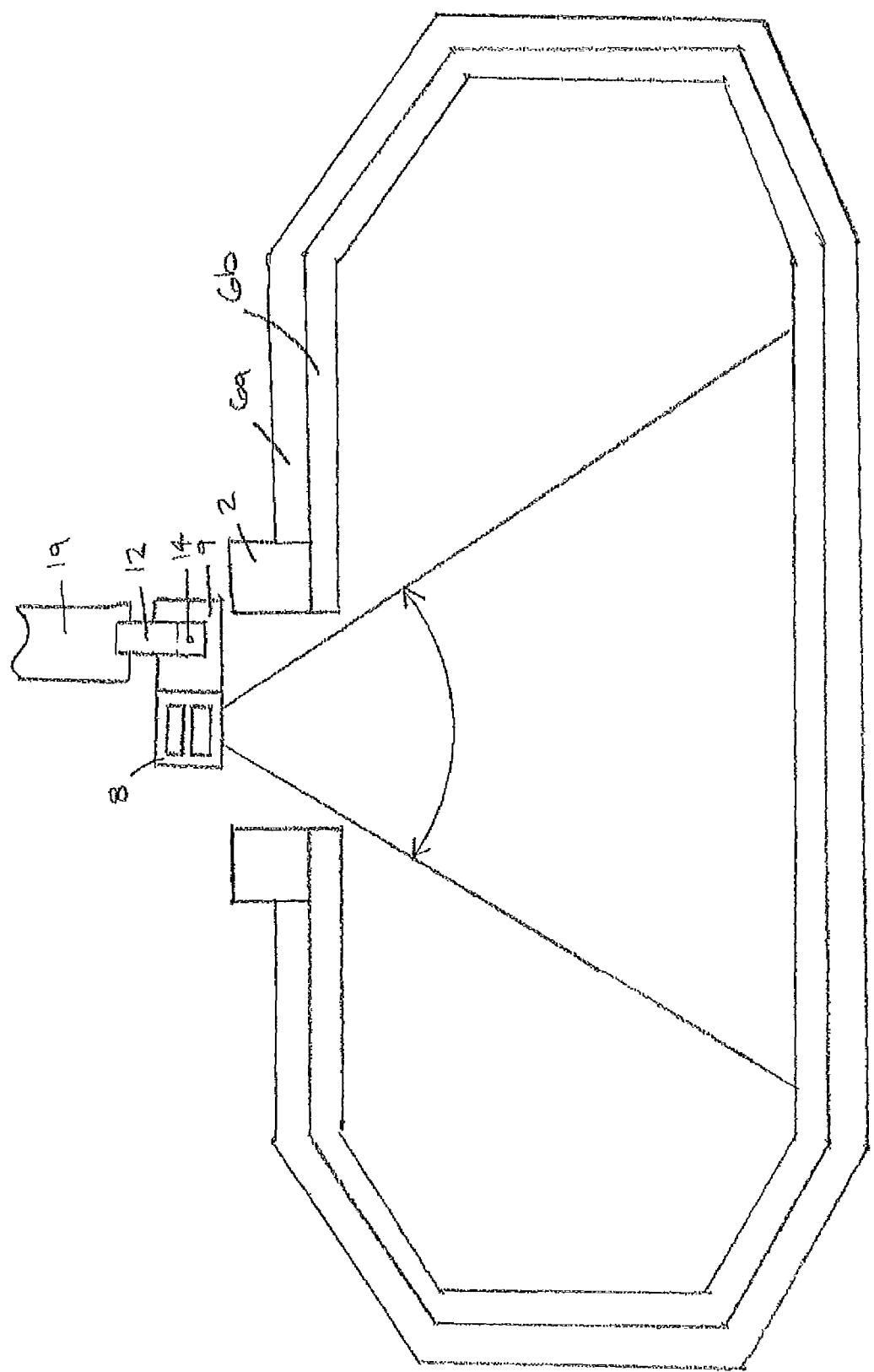
FIG. 10 shows schematically the embodiment of FIG. 8 of the system for measuring the inner space of a container illustrating the third position scan of the scanning means.
Figure 11:
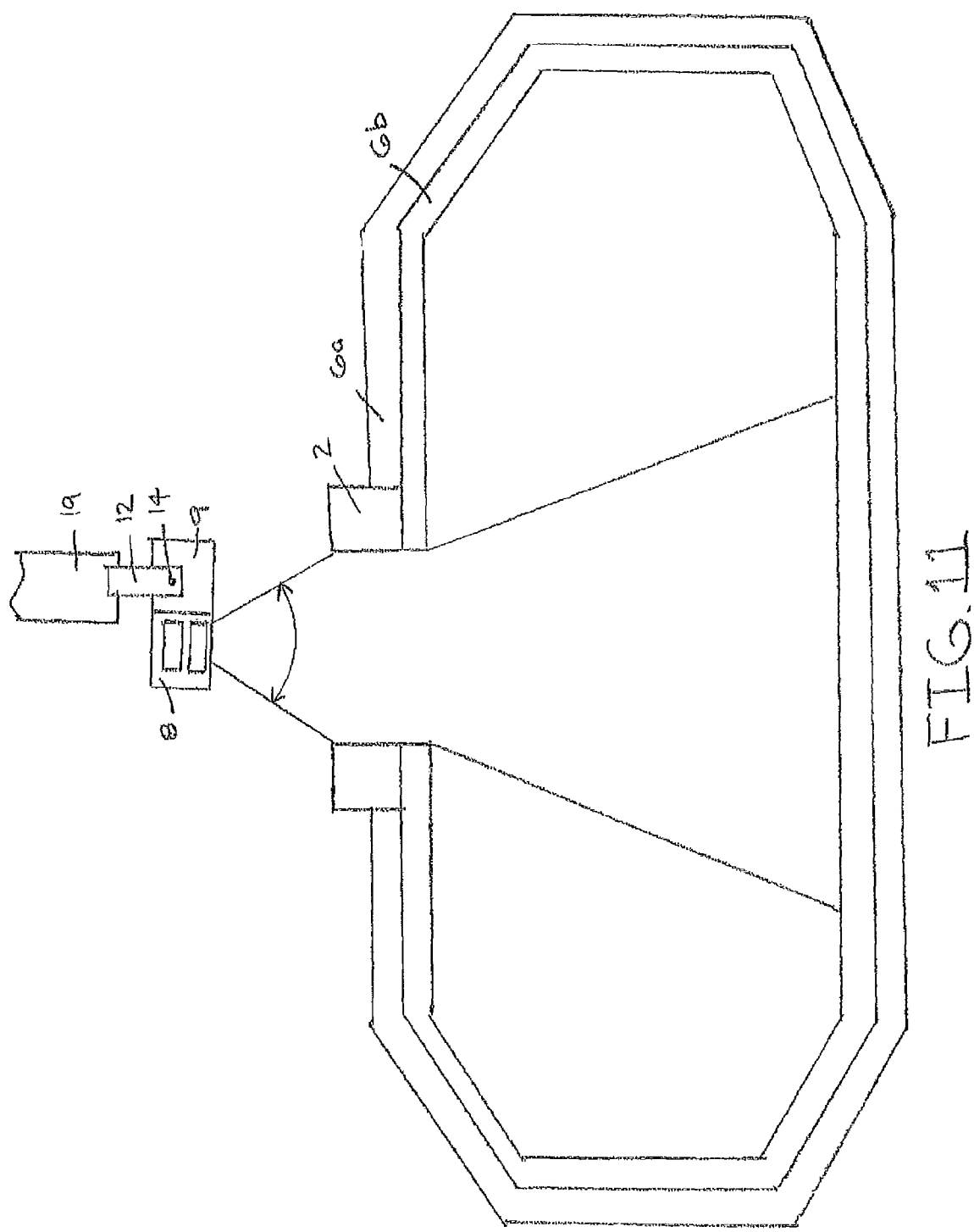
FIG. 11 shows schematically another variation of the third position scan the embodiment of FIG. 8 of the system for measuring the inner space of a container illustrating a variation of the third position scan of the scanning means.

Further, a third scan can be performed by moving the manipulator or tube 19 outside of the torpedo ladle 1 and placing the measuring head 8 at an angle from about 75 to 90 degrees, preferably 90 degrees relative to the axis V of the torpedo ladle 1 as seen in FIG. 10. The third scan permits scanning of portions of the bottom of the torpedo ladle 1. In addition to or as part of the third scan, the neck 2 of the torpedo ladle 1 can be scanned as seen in FIG. 11 which can include portions of the torpedo ladle 1 lining which were scanned previously.

Accordingly, the first scan, second scan and third scans are combined as described above to obtain a combined measurement of the contour of the lining.

It will be appreciated by those skilled in the art that the present invention can be embodied in other specific forms without departing from the essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

We claim:

1. A method for measuring wear in the refractory lining of a metallurgical vessel having a narrow opening comprising:
   providing a laser scanner for scanning the contour of the lining from different positions,
   providing a manipulator for moving the laser scanner to different positions outside and inside the vessel,
   scanning the contour of the lining using the laser scanner from a first position to obtain a first scan,
   scanning the contour of the lining using the laser scanner from a second position to obtain a second scan, wherein at least one of the first position and second position is located inside the vessel, and
   combining the first scan and second scan to obtain a combined measurement of the contour of the lining.

2. The method for measuring wear in the refractory lining of a metallurgical vessel according to claim 1 wherein the contour of the lining is scanned from only the first and second positions.

3. The method for measuring wear in the refractory lining of a metallurgical vessel according to claim 1 wherein the contour of the lining is scanned from the first position at which the manipulator positions the laser scanner within the metallurgical vessel at a first angle with respect to an axis of the metallurgical vessel, and from the second position within the metallurgical vessel at which the manipulator positions the laser scanner at a second angle with respect to the axis of the metallurgical vessel.

4. The method for measuring wear in the refractory lining of a metallurgical vessel according to claim 1 wherein the contour of the lining is scanned from the first position at which the manipulator positions the laser scanner within the metallurgical vessel and from the second position outside the metallurgical vessel at which the manipulator positions the laser scanner.

5. The method for measuring wear in the refractory lining of a metallurgical vessel according to claim 1 wherein the contour of the lining is scanned from at least three positions to obtain a scan from each of the at least three positions.

6. The method for measuring wear in the refractory lining of a metallurgical vessel according to claim 2 wherein the laser scanner is rotated from the first position to the second position approximately from 165 degrees to 195 degrees by a rotating means.

7. The method for measuring wear in the refractory lining of a metallurgical vessel according to claim 6 wherein the rotating means is a plate.

8. The method for measuring wear in the refractory lining of a metallurgical vessel according to claim 3 wherein the first angle from which the contour of the lining is scanned is +30 to +60 degrees with respect to the axis of the metallurgical vessel and the second angle is −30 to −60 degrees with respect to the axis of the metallurgical vessel.

9. The method for measuring wear in the refractory lining of a metallurgical vessel according to claim 3 wherein the first angle from which the contour of the lining is scanned is 0 to +15 degrees with respect to the axis of the metallurgical vessel and the second angle is +75 to +90 degrees with respect to the axis of the metallurgical vessel.

10. The method according to claim 1 wherein the metallurgical vessel having a narrow opening is a torpedo ladle.

11. A system for measuring wear in the refractory lining of a metallurgical vessel having a narrow opening comprising:
    a laser scanner for scanning the contour of the lining from a first position and a second position to obtain a scan of the contour of the lining from each of the first position and second position,
    a manipulator for moving the laser scanner from a first position to a second position, wherein at least one of the first position and second position is located inside the vessel, and
    a means for combining the first scan and second scan to obtain a combined measurement of the contour of the lining.

12. The system for measuring wear in the refractory lining of a metallurgical vessel according to claim 11 wherein the contour of the lining is scanned from only the first and second positions.

13. The system for measuring wear in the refractory lining of a metallurgical vessel according to claim 11 wherein the contour of the lining is scanned from the first position at which the manipulator positions the laser scanner within the metallurgical vessel at a first angle with respect to an axis of the metallurgical vessel, and from the second position within the metallurgical vessel at which the manipulator positions the laser scanner at a second angle with respect to the axis of the metallurgical vessel.

14. The system for measuring wear in the refractory lining of a metallurgical vessel according to claim 11 wherein the contour of the lining is scanned from the first position at which the manipulator positions the laser scanner within the metallurgical vessel and from the second position outside the metallurgical vessel at which the manipulator positions the laser scanner.

15. The system for measuring wear in the refractory lining of a metallurgical vessel according to claim 11 wherein the contour of the lining is scanned from at least three positions.

16. The system for measuring wear in the refractory lining of a metallurgical vessel according to claim 12 wherein the laser scanner is rotated from the first position to the second position approximately from 165 degrees to 195 degrees by a rotating means.

17. The system for measuring wear in the refractory lining of a metallurgical vessel according to claim 16 wherein the rotating means is a plate.

18. The system for measuring wear in the refractory lining of a metallurgical vessel according to claim 13 wherein the first angle from which the contour of the lining is scanned is +30 to +60 degrees with respect to the axis of the metallurgical vessel and the second angle is −30 to −60 degrees with respect to the axis of the metallurgical vessel.

19. The system for measuring wear in the refractory lining of a metallurgical vessel according to claim 13 wherein the first angle from which the contour of the lining is scanned is 0 to +15 degrees with respect to the axis of the metallurgical vessel and the second angle is +75 to +90 degrees with respect to the axis of the metallurgical vessel.

20. The system according to claim 11 wherein the metallurgical vessel having a narrow opening is a torpedo ladle.

\* \* \* \* \*